US010519420B2

(12) United States Patent
Harrell

(10) Patent No.: US 10,519,420 B2
(45) Date of Patent: *Dec. 31, 2019

(54) METHOD FOR OBTAINING STERILE HUMAN AMNIOTIC FLUID AND USES THEREOF

(71) Applicant: Carl Randall Harrell, Tarpon Springs, FL (US)

(72) Inventor: Carl Randall Harrell, Tarpon Springs, FL (US)

(73) Assignee: MAM Holdings of West Florida, L.L.C., Tarpon Springs, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/877,056

(22) Filed: Jan. 22, 2018

(65) Prior Publication Data

US 2018/0142204 A1   May 24, 2018

Related U.S. Application Data

(63) Continuation of application No. 14/275,086, filed on May 12, 2014, now abandoned.

(Continued)

(51) Int. Cl.
    *A61M 1/00*     (2006.01)
    *C12N 5/073*    (2010.01)
    *A61B 10/00*    (2006.01)

(52) U.S. Cl.
    CPC ........ *C12N 5/0605* (2013.01); *A61B 10/0048* (2013.01); *A61M 1/0011* (2013.01);
    (Continued)

(58) Field of Classification Search
    CPC ............ C12N 2/0605; A61B 10/0048; A61M 1/0011; A61M 2202/0437; A61M 2202/494
    (Continued)

(56) References Cited

U.S. PATENT DOCUMENTS

| 3,752,158 A * | 8/1973 | Kariher | A61M 1/0011 604/133 |
| 4,308,875 A * | 1/1982 | Young | A61B 17/4208 600/566 |

(Continued)

FOREIGN PATENT DOCUMENTS

| WO | 2004026244 | 4/2004 |
| WO | 2006091546 | 8/2006 |

OTHER PUBLICATIONS

Cianfarani, et al., "Placement growth factor in diabetic wound healing altered expression and therapeutic potential", Am J Pathol., 169(4):1167-82 (2006).

(Continued)

*Primary Examiner* — Andrew J Mensh
(74) *Attorney, Agent, or Firm* — Pabst Patent Group LLP

(57) ABSTRACT

Provided herein is a pre-Caesarean method for collecting amniotic fluid from a patient. A needle is inserted into the incision site for the future C-section, which may be under ultrasound guidance, through which the amniotic fluid is drawn under a low level suction and, optionally, gravity to a sterile collection container. The method encompasses filtering and/or irradiating the amniotic fluid to collect biomolecules of interest such as growth factors and/or stem cells. Also provided is the sterile amniotic fluid or filtrates thereof collected by the method described herein.

14 Claims, 8 Drawing Sheets

Related U.S. Application Data

(60) Provisional application No. 61/821,868, filed on May 10, 2013.

(52) U.S. Cl.
CPC ............... *A61M 2202/0437* (2013.01); *A61M 2202/0494* (2013.01)

(58) Field of Classification Search
USPC ......................................................... 604/319
See application file for complete search history.

(56) References Cited

U.S. PATENT DOCUMENTS

| | | | |
|---|---|---|---|
| 4,977,897 A * | 12/1990 | Hurwitz | A61B 8/0833 |
| | | | 600/461 |
| 5,000,192 A * | 3/1991 | Sealfon | A61B 10/0048 |
| | | | 600/573 |
| 5,219,576 A | 6/1993 | Chu | |
| 5,436,135 A | 7/1995 | Tayot | |
| 5,698,228 A | 12/1997 | Takai | |
| 5,997,896 A | 12/1999 | Carr, Jr. | |
| 7,871,646 B2 | 1/2011 | Ghinelli | |
| 7,928,280 B2 | 4/2011 | Hariri | |
| 8,372,439 B2 | 2/2013 | Daniel | |
| 2004/0057938 A1 | 3/2004 | Ghinelli | |
| 2004/0093046 A1 | 5/2004 | Sand | |
| 2005/0079147 A1 | 4/2005 | Delaey | |
| 2008/0064098 A1 * | 3/2008 | Allickson | C12N 5/0605 |
| | | | 435/366 |
| 2008/0181935 A1 | 7/2008 | Bhatia | |
| 2008/0181967 A1 * | 7/2008 | Liu | A61K 35/44 |
| | | | 424/583 |
| 2008/0286378 A1 * | 11/2008 | Behrens | A61K 35/50 |
| | | | 424/528 |
| 2009/0054350 A1 | 2/2009 | Tayot | |
| 2010/0318048 A1 | 12/2010 | Hoefinghoff | |
| 2011/0269667 A1 | 11/2011 | Shoseyov | |

OTHER PUBLICATIONS

Durham, et al., "Preliminary evaluation of vibriolysin, a novel proteolytic enzyme composition suitable for the debridement of burn wound eschar.", J Burn Care Rehabil., 14(5):544-51 (1993).

Kirker, et al., "Glycosaminoglycan hydrogel films as bio-interactive dressings for wound healing", Biomaterials, 23(17):3661-71 (2002).

\* cited by examiner

METHOD FOR OBTAINING STERILE HUMAN AMNIOTIC FLUID AND USES THEREOF

CROSS-REFERENCE TO RELATED APPLICATION

This nonprovisional application is a continuation of U.S. application Ser. No. 14/275,086, filed May 12, 2014, which claims benefit of and priority to U.S. provisional application No. 61/821,868, filed May 10, 2013, now abandoned, the entirety of which are hereby incorporated by reference.

BACKGROUND OF THE INVENTION

Field of the Invention

The present invention relates generally to the fields of the sterile obtention of a biological fluid and to the isolation and culture of biomolecules and cells from a biological fluid. More specifically, the present invention relates to a pre-cesarian surgical method for the sterile collection and filtering of amniotic fluid for the isolation of biomolecules and stem cells therefrom.

Description of the Related Art

Within the uterus of a pregnant woman, a growing fetus is surrounded and cushioned by amniotic fluid, a watery liquid within the amnion. Amniotic fluid is one of the main samples used for the medical examination of the pregnant woman and her fetus.

For gathering information about the fetus's health and development, particularly about the possibility of premature birth, amniotic fluid infection, fetal inflammation and infection, fetal damage, fetal maturity, fetal diseases and chromosomal abnormalities, and component analysis of amniotic fluid, amniocentesis (transabdominal amniotic fluid collection) is carried out by inserting a thin, hollow needle through the abdomen into the uterus and taking a small sample of amniotic fluid. Currently, abdominal puncture with a needle for collecting amniotic fluid from the uterus is used for various amniotic fluid tests including the identification of fetal abnormality and amniotic fluid infection. The insertion of the needle, however, entails the risk of complications and medical accidents, causing anxiety and pain to the pregnant woman.

Traditionally, during a Caesarean section, after cutting through the uterus, the amniotic fluid will be suctioned away and discarded to make a bit more room. Amniotic fluid contains electrolytes, growth factors, carbohydrates, lipids, proteins, amino acids, lactate, pyruvate, enzymes, hormones, and is a source of stem cells. While amniotic fluid cells can be obtained from a small amount of fluid during amniocentesis, these amounts are insufficient for a larger scale harvesting of biomolecules or culturing of the stem cells comprising amniotic fluid.

Thus, there is a recognized need in the art for an improved means for obtaining sterile amniotic fluid for use in research and the development of therapeutic products. Particularly, the prior art is deficient in methods for obtaining sterile human amniotic fluid with minimal or no risk to a pregnant woman or fetus by collecting the amniotic fluid prior to an elective Caesarean section. The present invention fulfills this longstanding need and desire in the art.

SUMMARY OF THE INVENTION

The present invention has been made keeping in mind the above problems occurring in the prior art, and an object of the present invention is to provide an apparatus for collecting amniotic fluid from the uterus, which can not only significantly decrease the risk occurring when a needle is directly inserted into the uterus in order to diagnose the possibility of premature birth, amniotic fluid infection, fetal inflammation and infection, fetal damage, fetal maturity, and fetus diseases and chromosomal abnormalities, and conduct component analysis on amniotic fluid, but also eliminate pain and anxiety caused by the direct insertion of the needle.

The present invention is directed to method of obtaining sterile human amniotic fluid from an individual. The method comprises inserting a blunt tip needle into the amniotic sac of said individual and attaching the blunt tip needle to a three-way stopcock. A Luer lock syringe is connected to the three-way stopcock and a first end of a length of sterile tubing is connected with the three-way stopcock. The amniotic fluid is collected sterilely through the blunt tip needle and sterile tubing into a collection container.

The present invention also is directed to sterile amniotic fluid collected by the method described herein.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
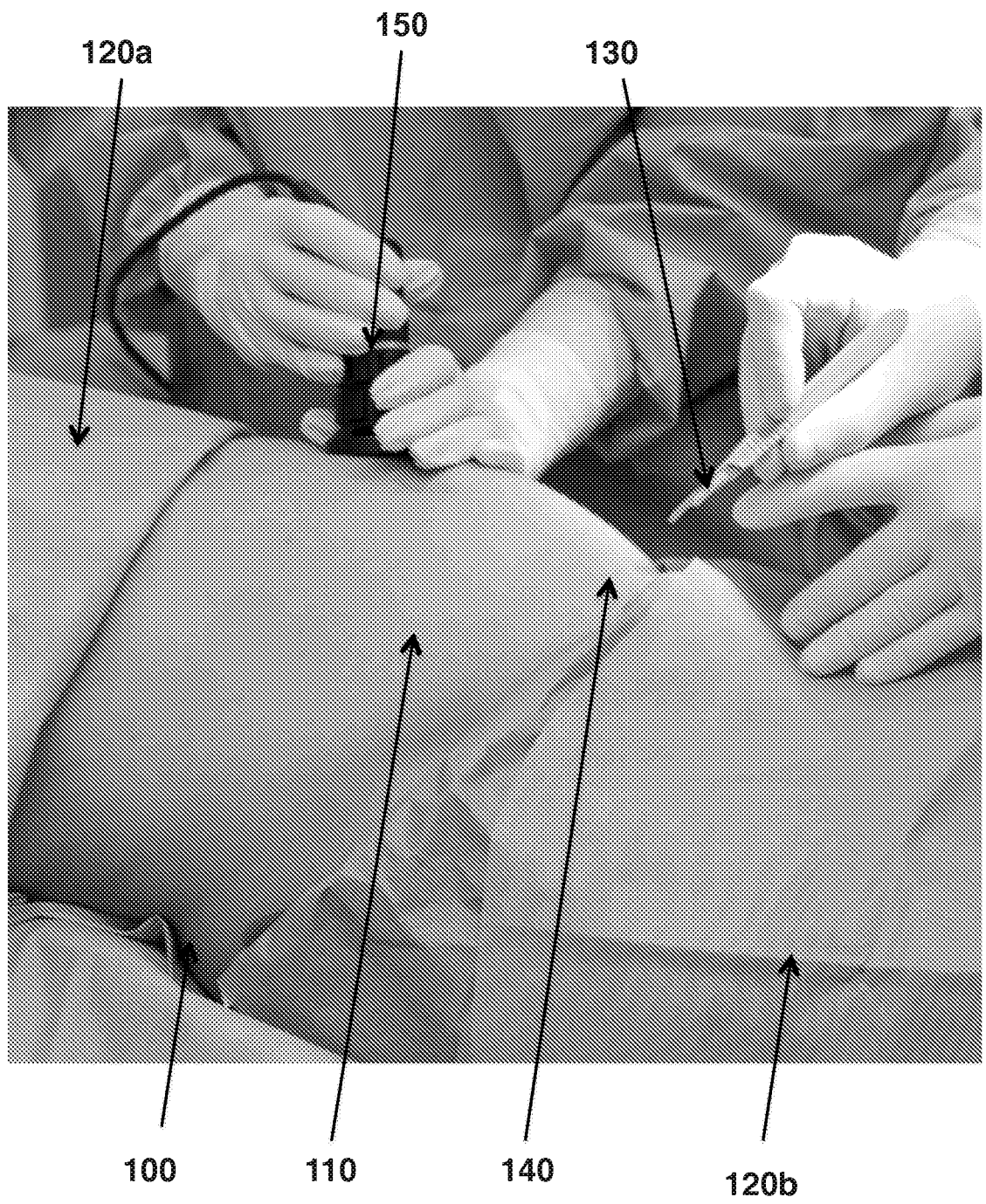
FIGS. 1A-1B depict the surgical set-up and patient from whom amniotic fluid can be collected.

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

In one embodiment of the present invention there is provided a method of obtaining sterile human amniotic fluid from an individual, comprising the steps of inserting a blunt tip needle into the amniotic sac of said individual; attaching the blunt tip needle to a three-way stopcock; connecting a Luer lock syringe to the three-way stopcock; connecting a first end of a length of sterile tubing with the three-way stopcock; and collecting sterilely said amniotic fluid through the blunt tip needle and sterile tubing into a collection container. In this embodiment and any aspects thereof collecting of the amniotic fluid may be performed under ultrasound guidance.

In this embodiment the sterile collection container may comprise a pump with a suction device. In one aspect of this embodiment suction device may be a low suction device or spring loaded low suction device. In another aspect the suction device may be fluidly connected to an internal balloon. Further to this aspect the method comprises manually pumping up the internal balloon in the sterile collection container using the low suction device to allow a low-level suction and collection of the amniotic fluid. In yet another aspect the sterile collection container may comprise an inlet. Further to this particular aspect the method comprises connecting a second end of the tubing to the inlet of the sterile collection container.

In yet another aspect of this embodiment the sterile collection container may comprise a vent having a cap. Further to this aspect the method comprises sterilizing the amniotic fluid by filtration. In this further aspect the sterilizing step may comprise filtering the amniotic fluid through 100 μm filters to remove large particles while retaining stem cells to obtain prefiltered amniotic fluid.

Alternatively, the sterilizing step may comprise passing prefiltered amniotic fluid through a filter having a size of from about 10 μm to about 1 μm so to remove cells and large particles to obtain a micron filtrate. Further to this alternative step the method comprises passing the micron filtrate through a filter having a size of about 0.45 μm to obtain a submicron filtrate. Further still the method comprises irradiating the submicron filtrate to obtain an irradiated filtrate. Further still the method comprises passing the irradiated filtrate through a filter having a size of about 0.22 μm to achieve sterile amniotic fluid. In this irradiating step irradiation may be by e-beam irradiation or gamma ray irradiation.

In another embodiment of the present invention there is provided a sterile amniotic fluid prepared by the method as described supra. In this embodiment the sterile amniotic fluid may comprise a filtrate containing biomolecules selected via filtration. Representative examples of biomolecules are growth factors or stem cells or a combination thereof.

Provided herein is a process for obtaining sterile human amniotic fluid in quantity and the human amniotic fluid so collected. A collection procedure is performed in a sterile operating room environment during an elective C-section. Utilizing the incision site immediately prior to performing the C-section and with ultrasound guidance to protect the fetus and mother provides a minimal or no risk environment for collection. Collection is achieved via a low level suction established within a collection container and/or via gravity. The collected sterile amniotic fluid contains biomolecules and other biomaterials, such as growth factors and stem cells which provide raw starting materials for the development of therapeutics. The collected sterile amniotic fluid also can be filtered for such biomolecules and biomaterials.

A collection system for the sterile collection of amniotic fluid generally comprises fluid collection components and a fluid container component. The collection system is assembled such that amniotic fluid is drawn from a pregnant women through the fluid collection components, such as a needle and tubing combination, to the container component. The container component comprises a means for pumping up an internal balloon to generate a low level suction to improve flow of the amniotic fluid.

The present invention describes several ways by which a person having ordinary skill in this art could process sterile products collected in amniotic fluid by filtration. Typically, one would perform pre-filtration such as with, for example, 100 μm filters (low protein binding filter) to remove large particles but retain the stem cells. The size of mesenchymal stem cells is ~30 μm. Next, one would perform pre-filtration with 10 to 1 μm filters (low protein binding filter) to remove cells and large particles. Submicron filtration would then be conducted with 0.45 μm filters (low protein binding filter), two in a series connection, to remove gross contaminates. Under this condition, soluble collagen and growth factors will pass through this filter to achieve a semi-sterile condition, very low bioburden counts. If under a strict aseptic operation condition, a $10^{-3}$ sterility assurance level could be achieved.

Further, a $10^{-6}$ sterility assurance level could be achieved by e-beam or gamma ray irradiation with low dose and frozen conditioning after final packaging. Submicron filtration would then be conducted with a 0.22 μm filter (low protein binding filter) at the end and sterile packaging to achieve a sterile product. One would monitor the filtrate after each filtration step to determine which components were removed and then to determine which process to use to achieve the desirable product.

Using the methodology described herein, it is possible to filter the amniotic fluid. One may use membrane filters comprising or made of hydrophilic polyethersulphone (PES) to filter protein solutions. Filter disks for small volumes and different sizes of cartridges for larger volumes such 1 litre and more. Hydrophobic membranes like PTFE which are designed for liquids devoid of proteins should not be used. Start with a prefilter to remove protein aggregates and precipitates in suspension (AP20 can be used). Next, centrifugation is conducted at 5000 to 8000 rpm for at least 30 minutes may be an easier alternative to clarify small volumes of few litres or less. If one directly uses a 0.6/0.2 μm filter, after prefiltration, one may experience slow filtration rates and the flow will stop too quickly. It may be desirable to make intermediate filtration steps using 1.2 μm and 0.8 μm membranes. Typically, a final filtration through 0.2 μm is necessary to get the sterility and produce a sterile amniotic fluid for injections.

As described below, the invention provides a number of advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

Figure 1B:
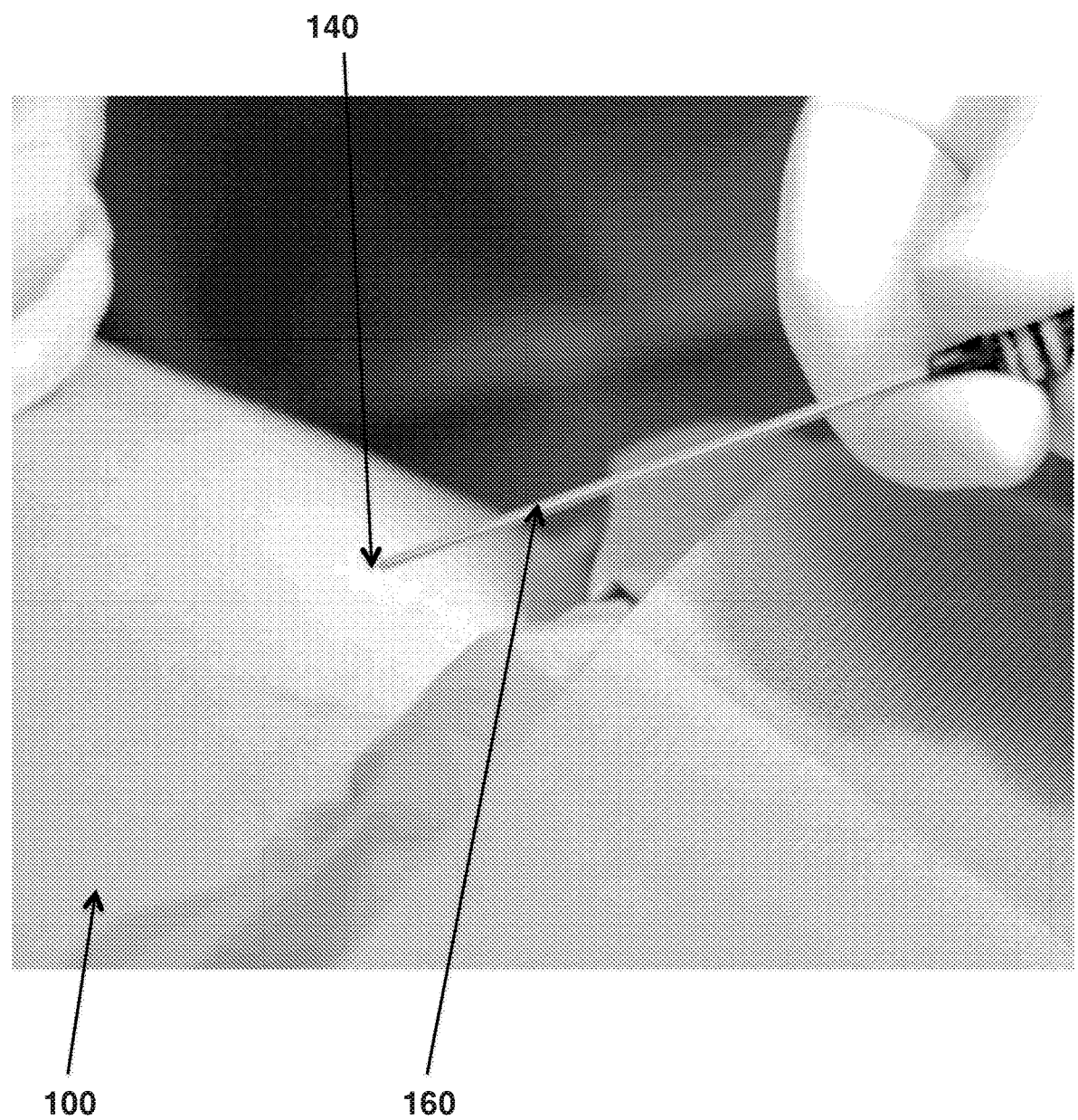

FIG. 1A shows a pregnant patient 100 prepped for a Caesarean section (C-section). The abdomen 110 is cleaned and prepped and the patient is draped at 120a,b as well-known and standard in the art. A number 15 scalpel blade 130 is used at the site of the future C-section incision at 140 to penetrate the dermis. Simultaneously, an ultrasound 150 is performed to protect the fetus and the mother. FIG. 1B illustrates how a blunt tip needle 160, to avoid any blood vessel penetration or damage to fetus or mother 100, is inserted at the incision site 140.

Figure 2A:
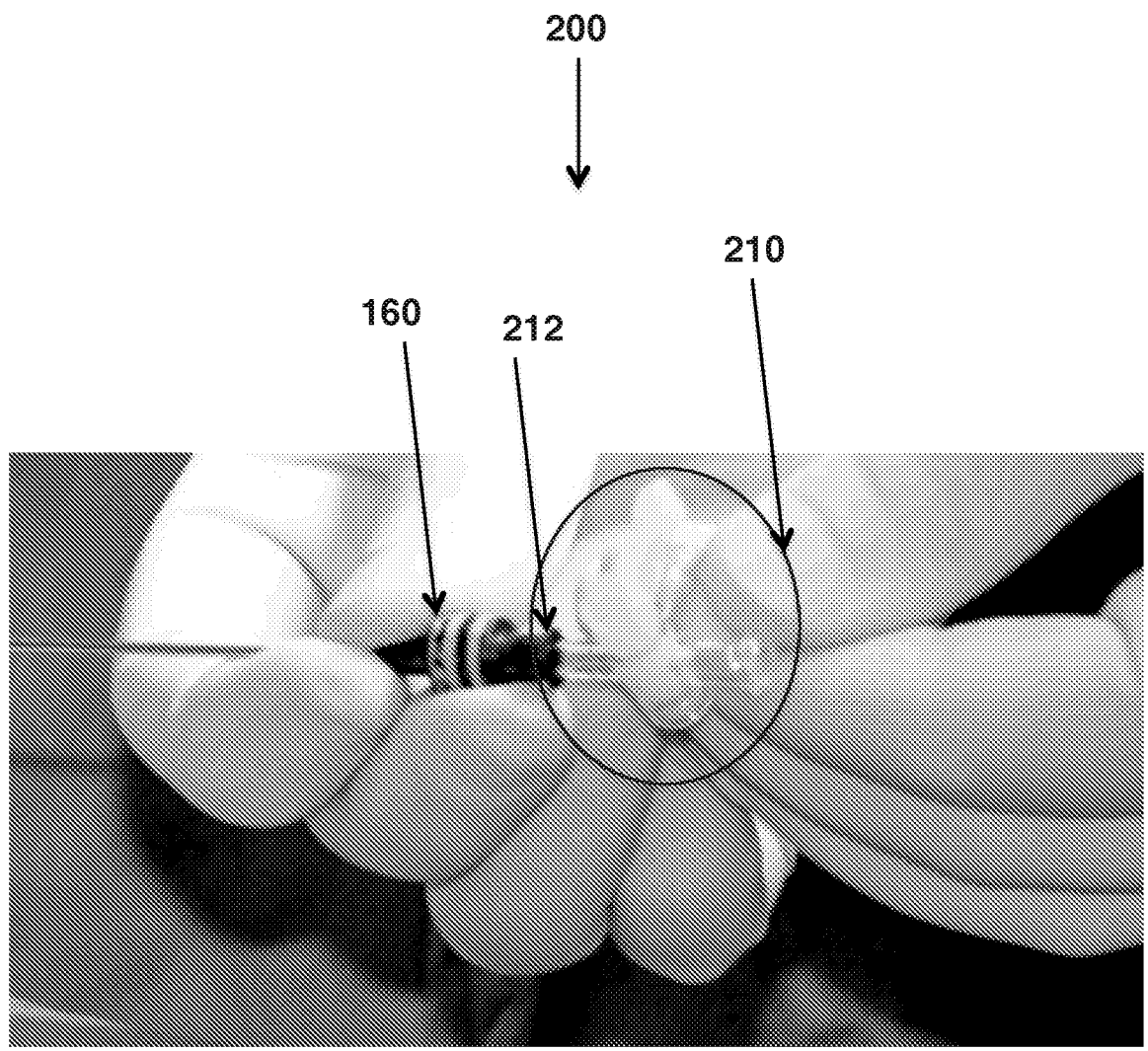
FIGS. 2A-2C depict the steps to assemble the components for the fluid collection portion of the collection system.

FIG. 2A illustrates the connection of the blunt tip needle 160 to a three-way stopcock 210 (circled) at connection 212.

Figure 2B:
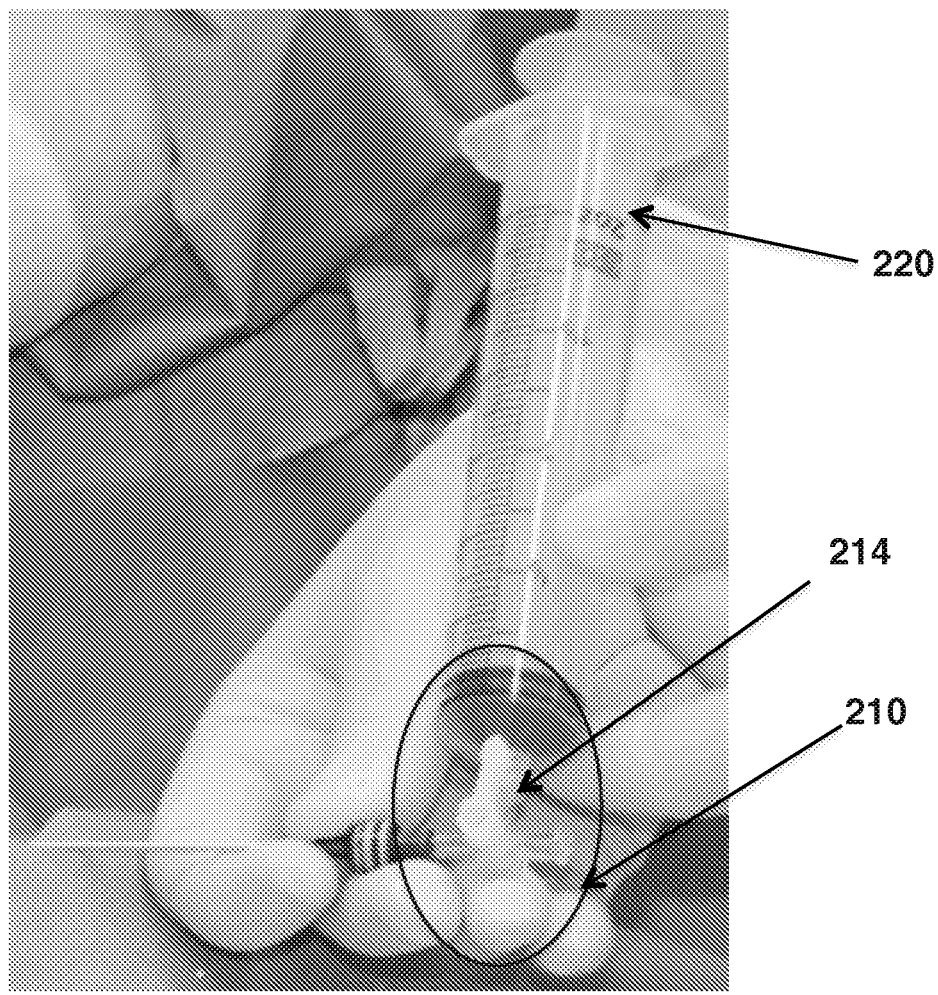

FIG. 2B illustrates the connection of a 60 cc Luer lock syringe 220 connected to the three-way stopcock at the Luer Lock connection 214. The syringe is utilized to clear any obstruction in the tubing 230 (see FIG. 2C).

Figure 2C:
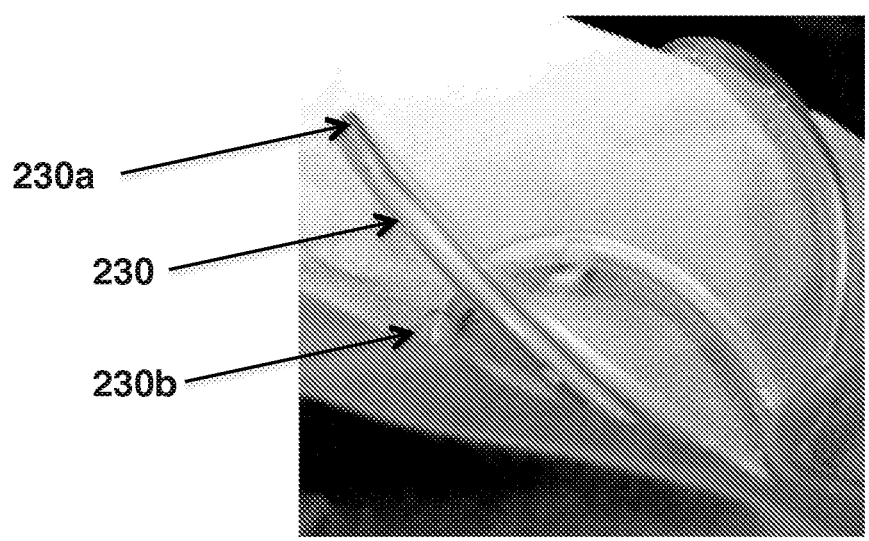

FIG. 2C shows a length of sterile tubing 230 with a first end 230a and a second end 230b. The first end is connected to the three-way stopcock 210 at connection 214. This arrangement with the syringe allows the amniotic fluid to be collected sterilely through the blunt tip needle 160 and sterile tubing 230 to a collection container 300 (see FIG. 3A) under ultrasound 150 guidance.

Figure 3A:
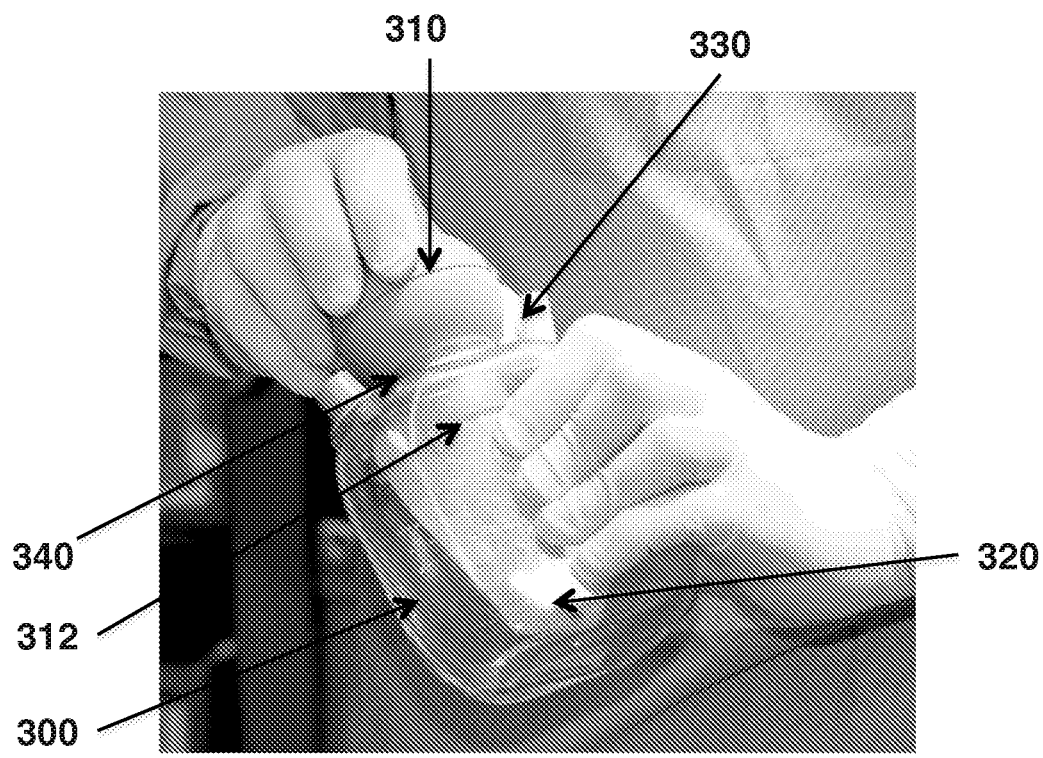
FIGS. 3A-3D depict the steps to prepare the container for collection of the amniotic fluid and to attach the assembled needle portion thereto.

FIG. 3A shows a sterile collection container 300 with a collection volume of about 400 cc to about 800 cc for sterile collection of the amniotic fluid specimen. The collection container comprises a pump with a low suction device 310 or spring loaded low suction device and an internal balloon 320 fluidly connected to the suction device at 312. The collection container comprises an inlet 330 and a vent 340 having a cap 342 (see FIG. 3B).

Figure 3B:
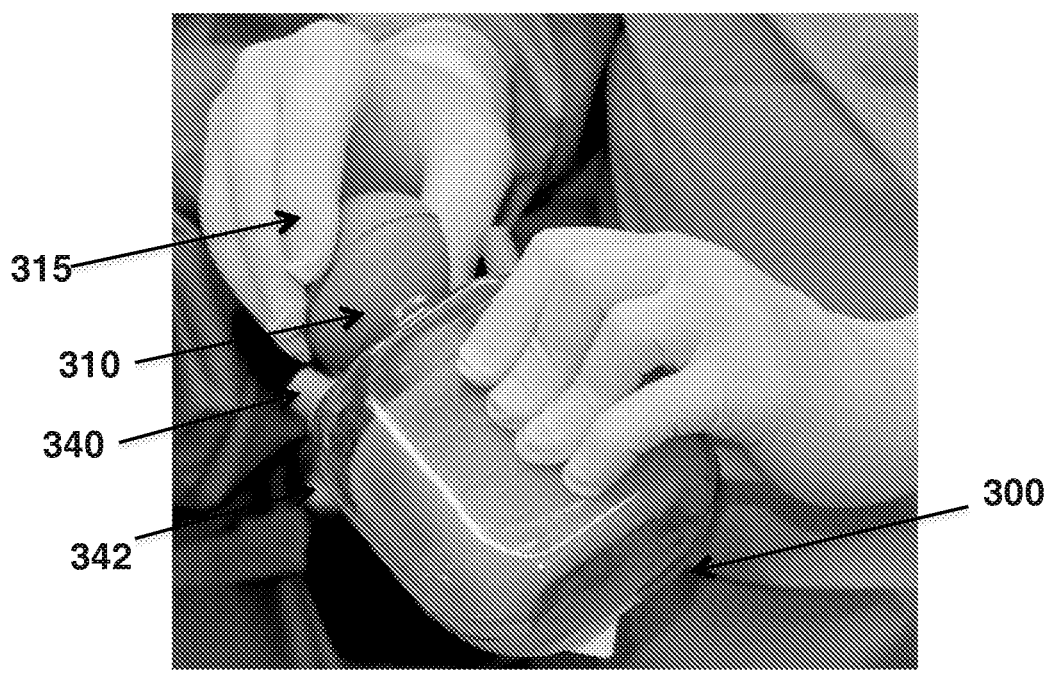

FIG. 3B demonstrates manually pumping up at 315 the internal balloon 320 in the sterile collection container 300 with the low suction device 310 which allows a low level suction for more efficient sterile collection of the amniotic fluid specimen. The cap 342 to the vent 340 is removed during pumping.

Figure 3C:
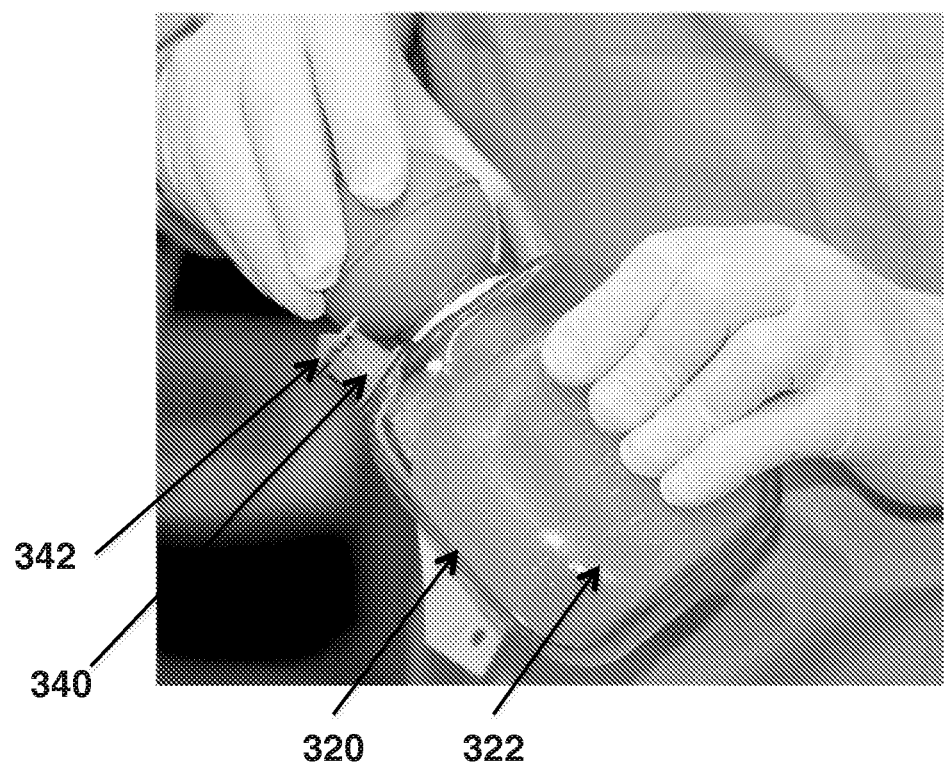

FIG. 3C shows the internal balloon 320 fully expanded at 322. Once maximum suction is obtained by full expansion of the internal balloon the vent 340 is resealed with the cap 342.

Figure 3D:
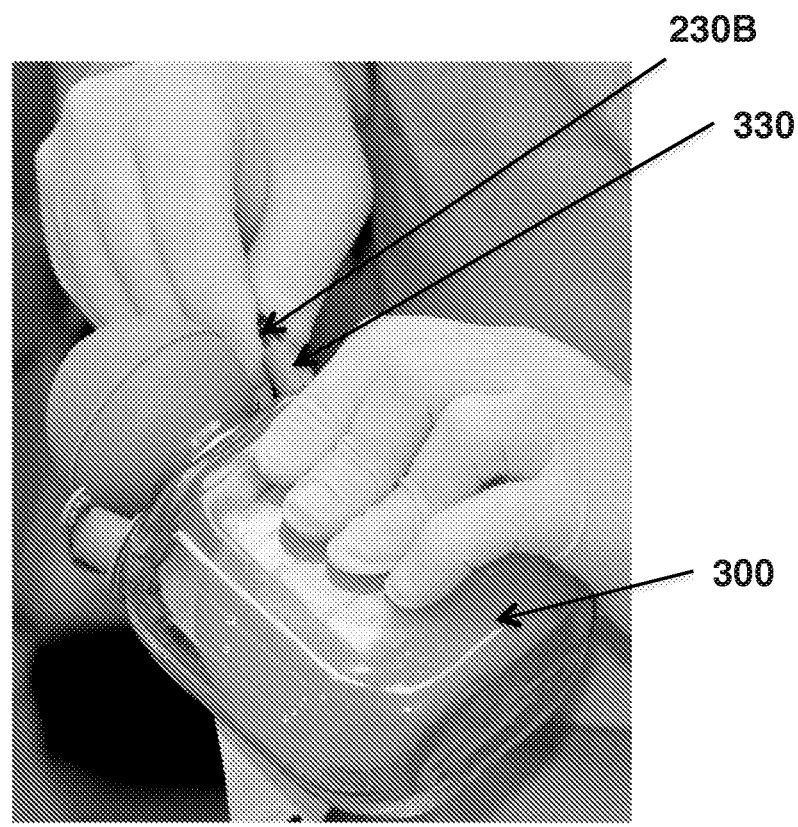

FIG. 3D demonstrates connecting the second end 230b of the tubing 230 to the inlet 330 of the collection container 300.

Figure 4:
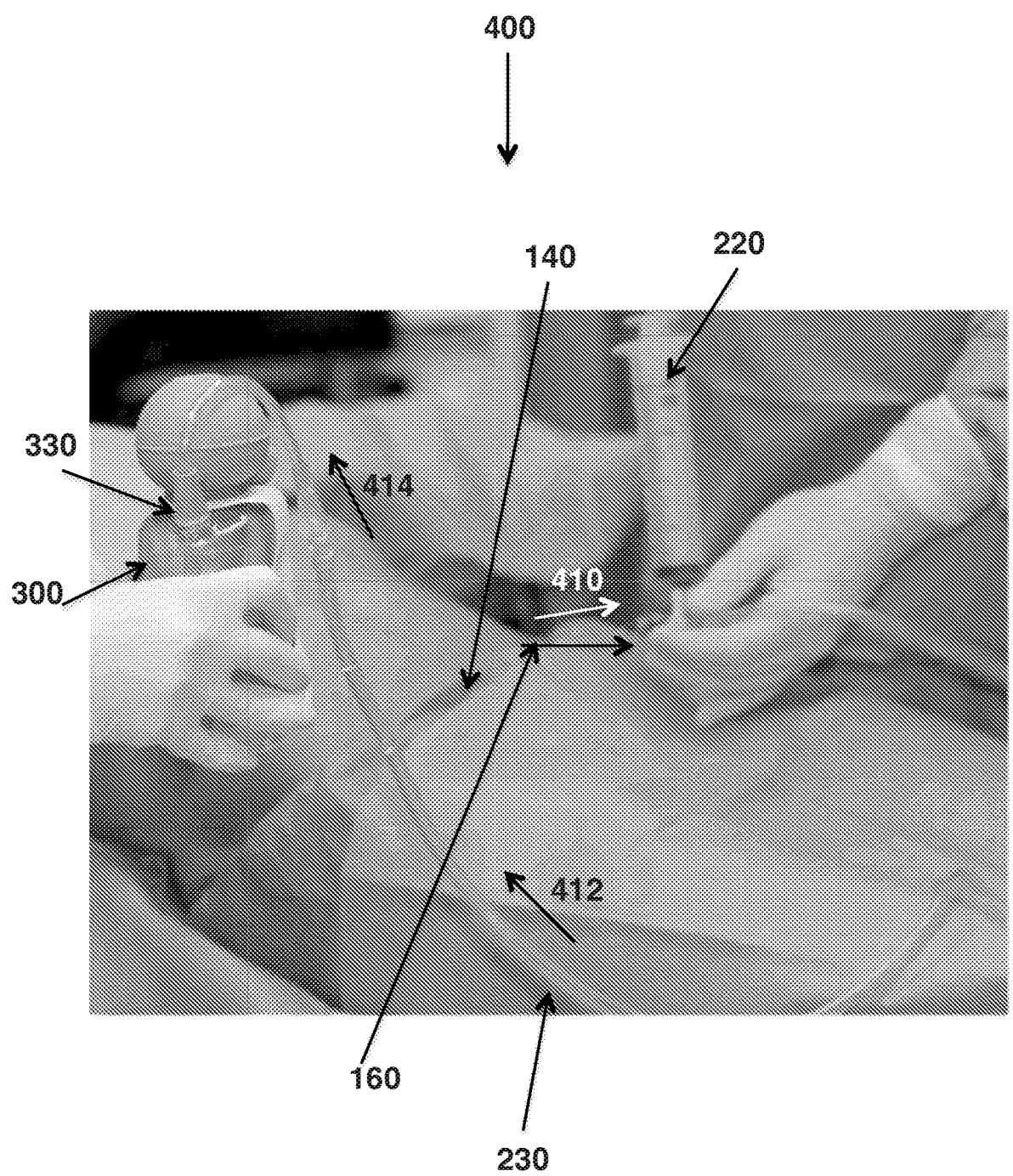
FIG. 4 depicts the assembled collection system.

FIG. 4 illustrates the fully connected collection system 400 which can now be utilized to obtain the sterile amniotic fluid from the patient. The low level suction in the inflated internal balloon 320 assists in drawing the amniotic fluid through the blunt tip needle 160 at 410 upon its ultrasound guided insertion into incision 140, through the tubing 230 at 412 and into the sterile collection container 300 via inlet 330 at 414. The syringe 220 is useful to remove a blockage, for example air, from the tubing if it occurs and keeps the collection system closed. The collection container can be placed on the floor to improve gravity drainage in addition to the low suction of the collection device.

Figure 5:
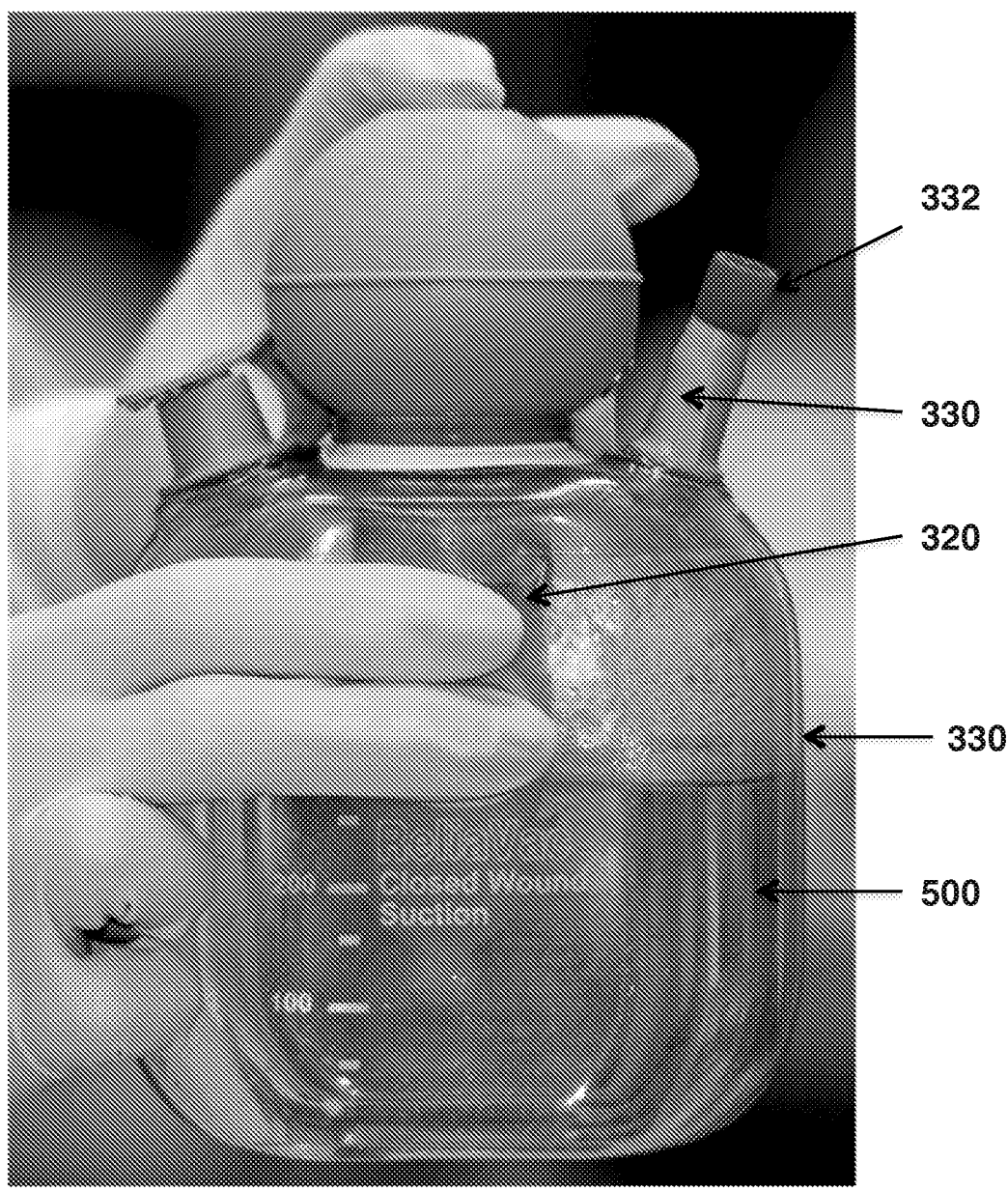
FIG. 5 depicts the sealed collection container with the amniotic fluid.

FIG. 5 shows the sterile connection container 300 after the amniotic fluid 500 collection is completed. A sterile top 332 seals the inlet 330 after the tubing 230 (see FIG. 4) has been removed. As the amniotic fluid is collected, the internal balloon 320 deflates. The completely closed sterile collection container is now ready to be refrigerated and shipped to a processing facility.

One skilled in the art will appreciate readily that the present invention is well adapted to carry out the objects and obtain the ends and advantages mentioned, as well as those objects, ends and advantages inherent herein. The present devices, systems and methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of obtaining sterile filtered acellular non-irradiated human amniotic fluid comprising bioactive growth factors, the method comprising serially filtering the human amniotic fluid, the steps of the method comprising:
   collecting amniotic fluid under sterile conditions,
   removing cells and particulate matter from the human amniotic fluid by centrifuging or depth filtering the human amniotic fluid to obtain cell-free amniotic fluid, and
   serially filtering the cell-free amniotic fluid through multiple filters selected from the group consisting of filters with a pore size of 100 μm, 1.2 μm, 1.0 μm, 0.8 μm, 0.6, 0.45 μm, 0.22 μm and 0.2 μm to obtain a sterile filtered acellular human amniotic fluid without irradiation.

2. The method of claim 1, wherein collecting of the amniotic fluid is performed under ultrasound guidance.

3. The method of claim 1, wherein the step of collecting the amniotic fluid comprises the use of a sterile collection container, wherein the sterile collection container comprises a pump with a suction device.

4. The method of claim 3, wherein the suction device is a low suction device or spring loaded low suction device.

5. The method of claim 3, wherein the suction device is fluidly connected to an internal balloon.

6. The method of claim 5, further comprising manually pumping up the internal balloon in the sterile collection container using the low suction device to allow a low-level suction and collection of the amniotic fluid.

7. The method of claim 3, wherein the sterile collection container comprises an inlet.

8. The method of claim 7, further comprising connecting a second end of the tubing to the inlet of the sterile collection container.

9. The method of claim 3, wherein the sterile collection container comprises a vent having a cap.

10. The method of claim 9, wherein the vent is resealed after full expansion of the internal balloon.

11. The method of claim 1, comprising filtering the decellularized amniotic fluid through a 100 μm filter to remove large particles.

12. The method of claim 1, wherein the decellularized amniotic fluid is serially passed through filters having a size of between about 10 μm and about 1 μm to remove cells.

13. The method of claim 12, wherein the amniotic fluid is filtered through one or more filters selected from the group consisting of filters having a size of about 0.8 μm, 0.6 μm, 0.45 μm, 0.22 μm and 0.2 μm .

14. Sterile filtered non-irradiated acellular human amniotic fluid prepared by the method of claim 1.

* * * * *